United States Patent [19]

Hinckfuss et al.

[11] Patent Number: 5,197,989
[45] Date of Patent: Mar. 30, 1993

[54] TWO STAGE JOINT PROSTHESIS

[76] Inventors: Bruce W. Hinckfuss, 246 La Trobe Terrace, Geelong, Victoria; Rodney B. Brink, 337 Ryrie Street, Geelong, Victoria 3220; Gregory Sapozhnikov, 5/308 Hampton Street, Hampton, Victoria, all of Australia

[21] Appl. No.: 642,713

[22] Filed: Jan. 17, 1991

Related U.S. Application Data

[63] Continuation of Ser. No. 240,141, Sep. 2, 1988, abandoned.

[30] Foreign Application Priority Data

Sep. 3, 1987 [AU] Australia ................ P14135/87

[51] Int. Cl.⁵ .............................................. A61F 2/34
[52] U.S. Cl. .......................................... 623/23; 623/18
[58] Field of Search ............... 623/16, 18, 19, 20, 623/22, 23

[56] References Cited

U.S. PATENT DOCUMENTS

| | | | |
|---|---|---|---|
| 3,840,904 | 10/1974 | Tronzo | 623/22 |
| 4,187,559 | 2/1980 | Grell | 623/18 |
| 4,488,319 | 12/1984 | von Recum | 623/23 |
| 4,769,041 | 9/1988 | Morscher | 623/22 |

FOREIGN PATENT DOCUMENTS

| | | | |
|---|---|---|---|
| 3310944 | 11/1984 | European Pat. Off. | 623/22 |
| 0134105 | 3/1985 | European Pat. Off. | 623/22 |
| 0158534 | 10/1985 | European Pat. Off. | 623/22 |
| 0179626 | 4/1986 | European Pat. Off. | 623/18 |
| 0208578 | 1/1987 | European Pat. Off. | |
| 2854334 | 6/1980 | Fed. Rep. of Germany | |
| 3216538 | 11/1983 | Fed. Rep. of Germany | 623/22 |
| 8602261 | 4/1986 | PCT Int'l Appl. | 623/22 |

*Primary Examiner*—David Isabella
*Attorney, Agent, or Firm*—Trask, Britt & Rossa

[57] ABSTRACT

Insertable structure of appropriate shape and strength to receive eventually at least one second stage component thus creating a composite with sufficient strength and fixation to the bones remaining adjacent the joint replaced by the prosthesis to take the place of the natural elements of the joint being replaced, the first stage component or components including connection means designed to cooperate with connection means of a second stage component, the second stage component forming or supporting at least in part, a bearing surface of the joint prosthesis, and designed so as to be disconnectable as an initial stage of a revision procedure. Hip joint prostheses and methods of total hip arthroplasty are specifically disclosed.

13 Claims, 6 Drawing Sheets

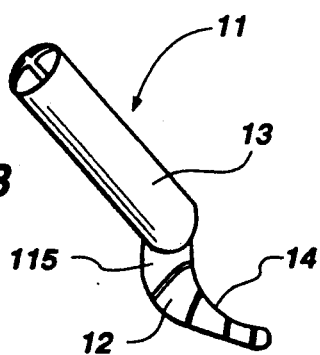
Fig. 2B
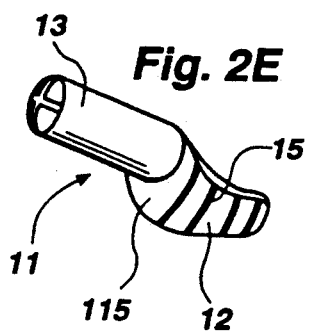
Fig. 2E
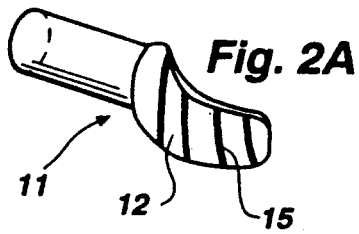
Fig. 2A
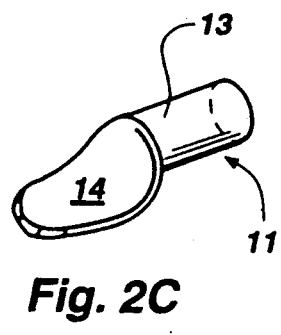
Fig. 2C
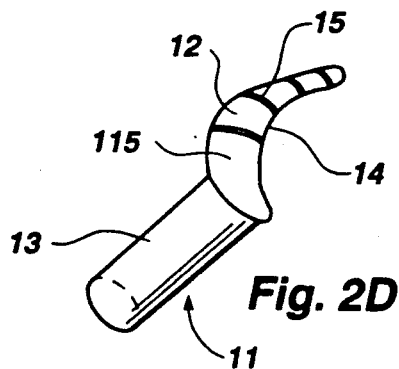
Fig. 2D
Fig. 3B
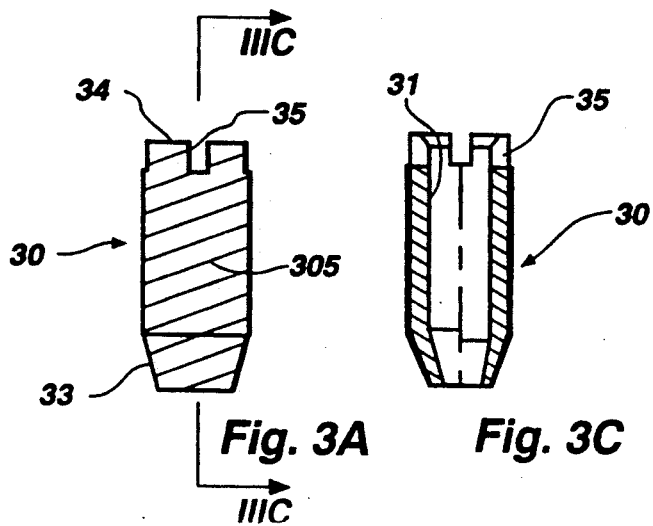
Fig. 3A  Fig. 3C

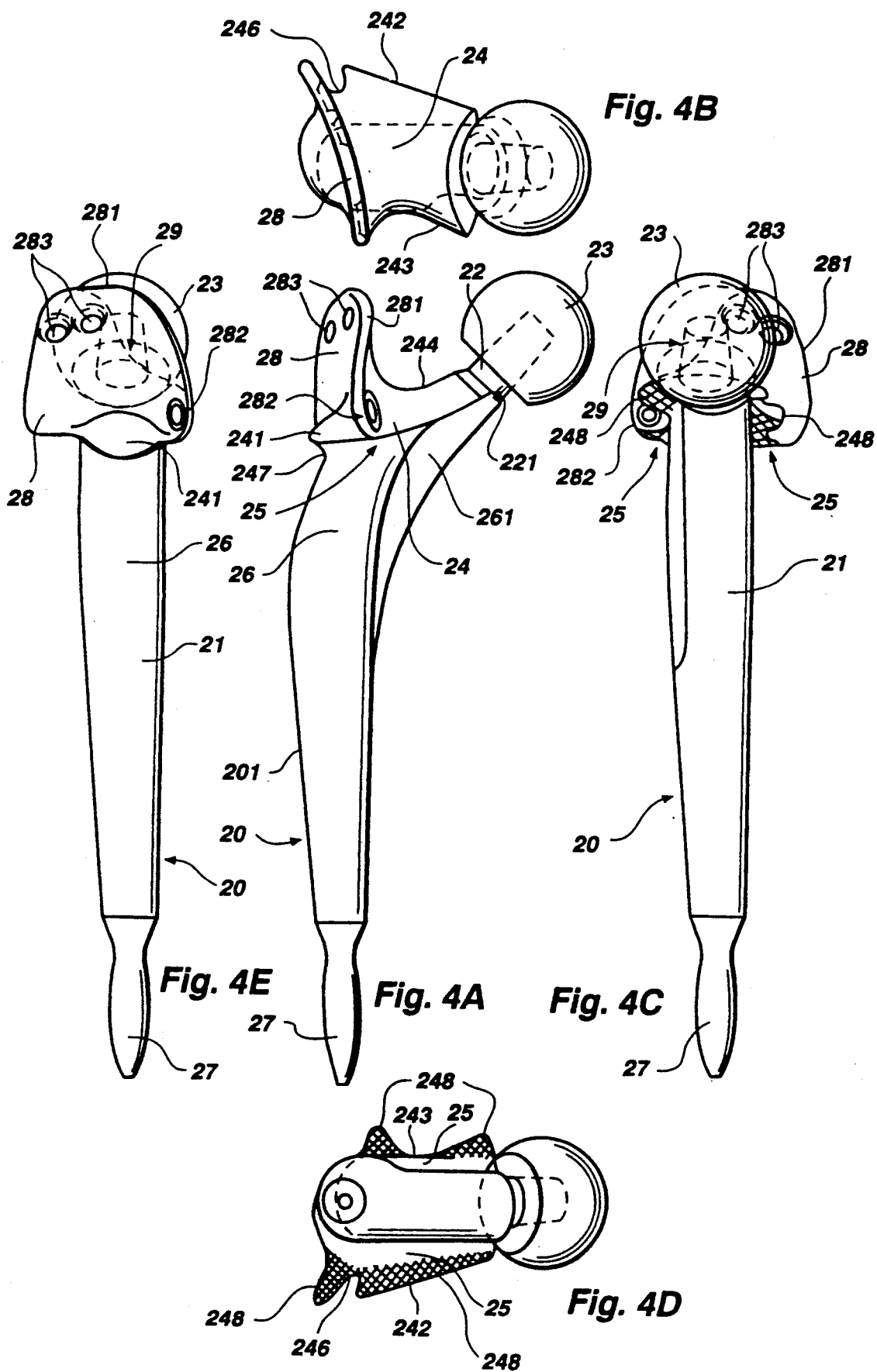

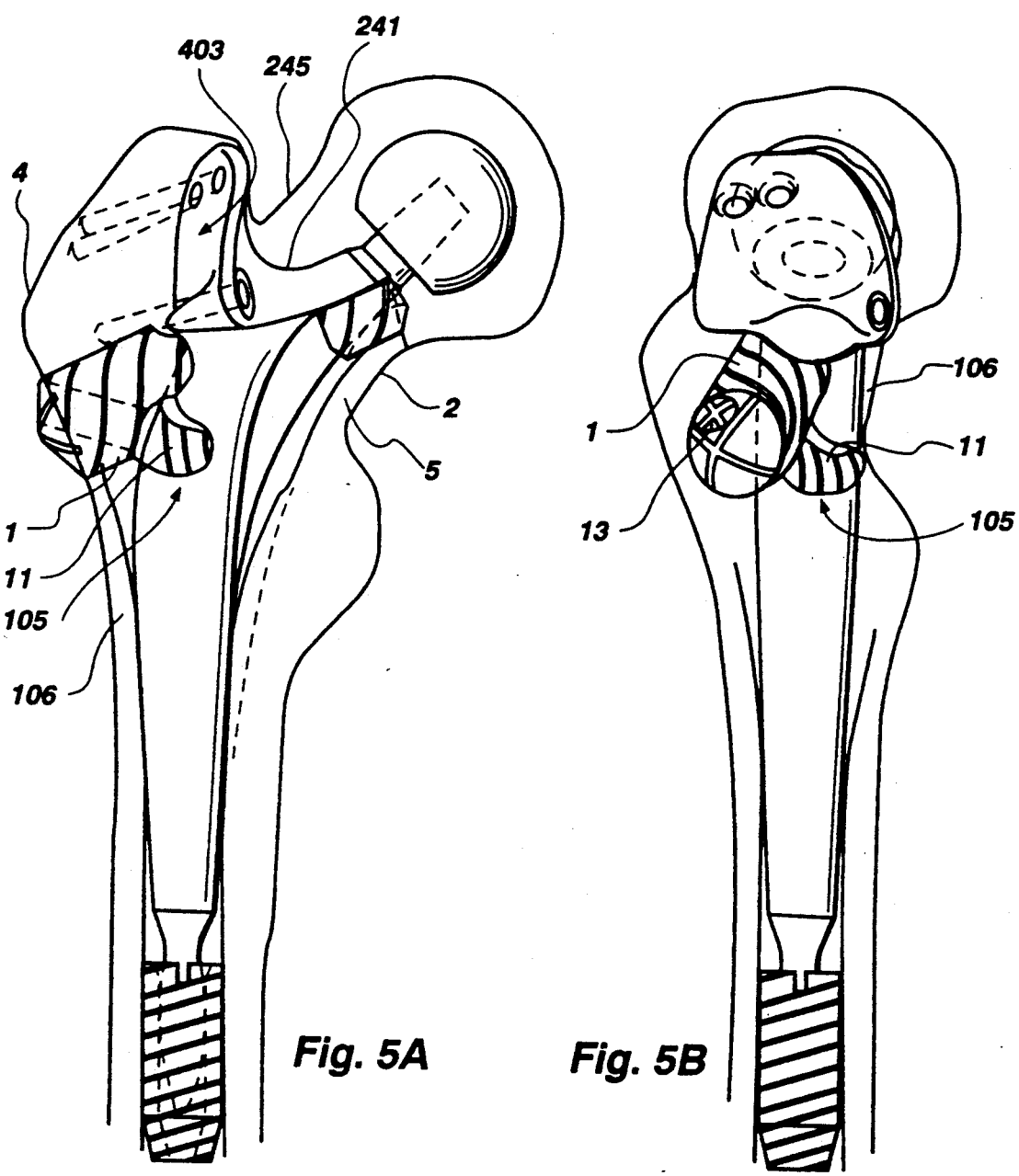
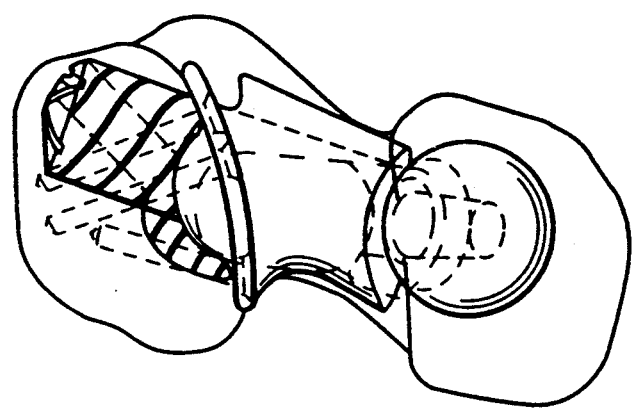
Fig. 5A   Fig. 5B
Fig. 5C

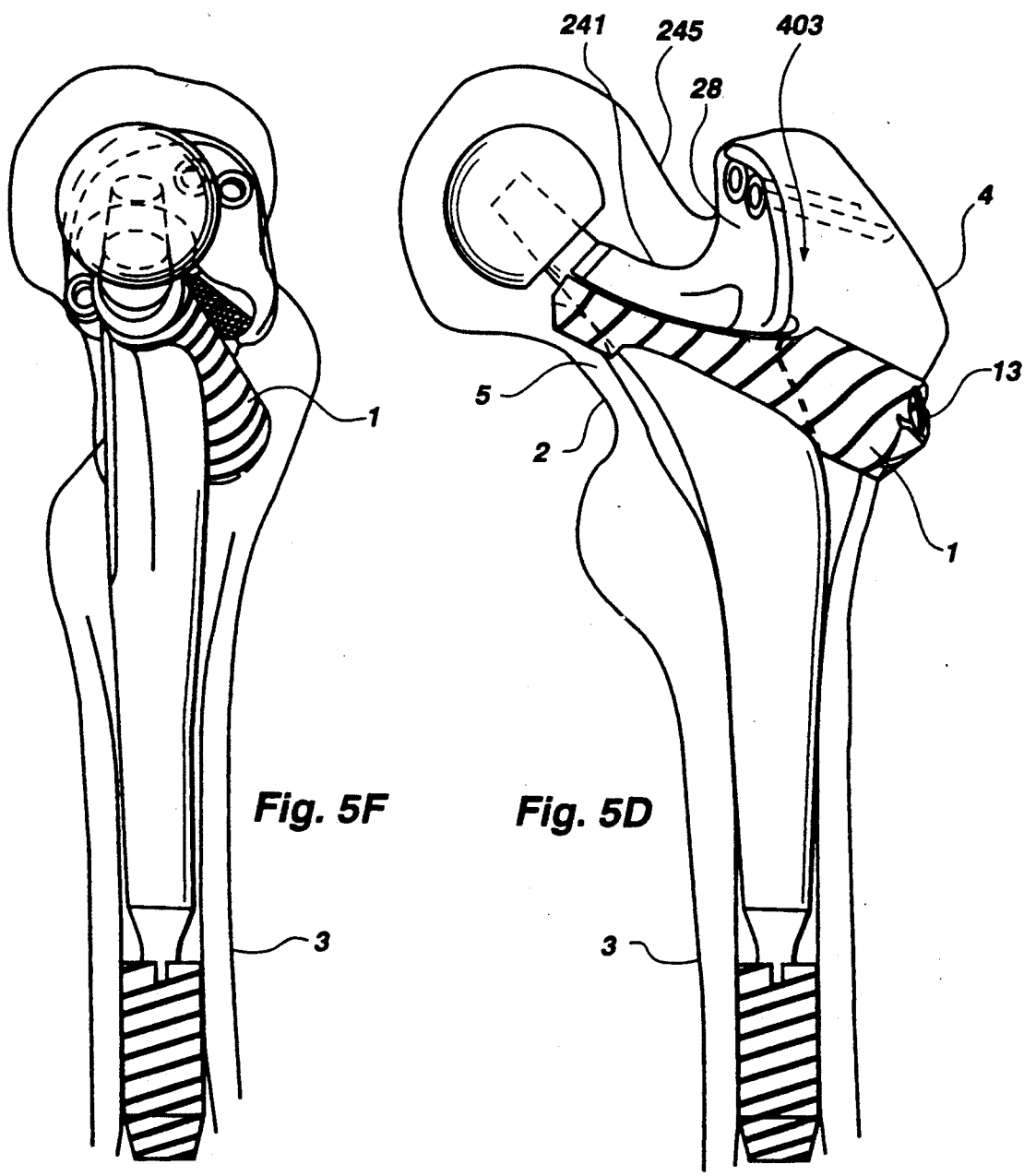
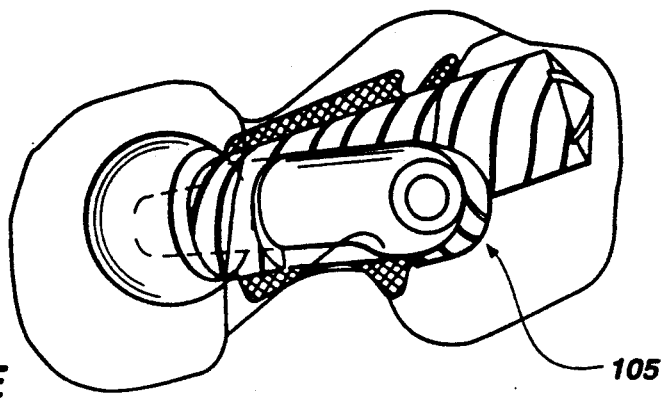
Fig. 5F    Fig. 5D
Fig. 5E

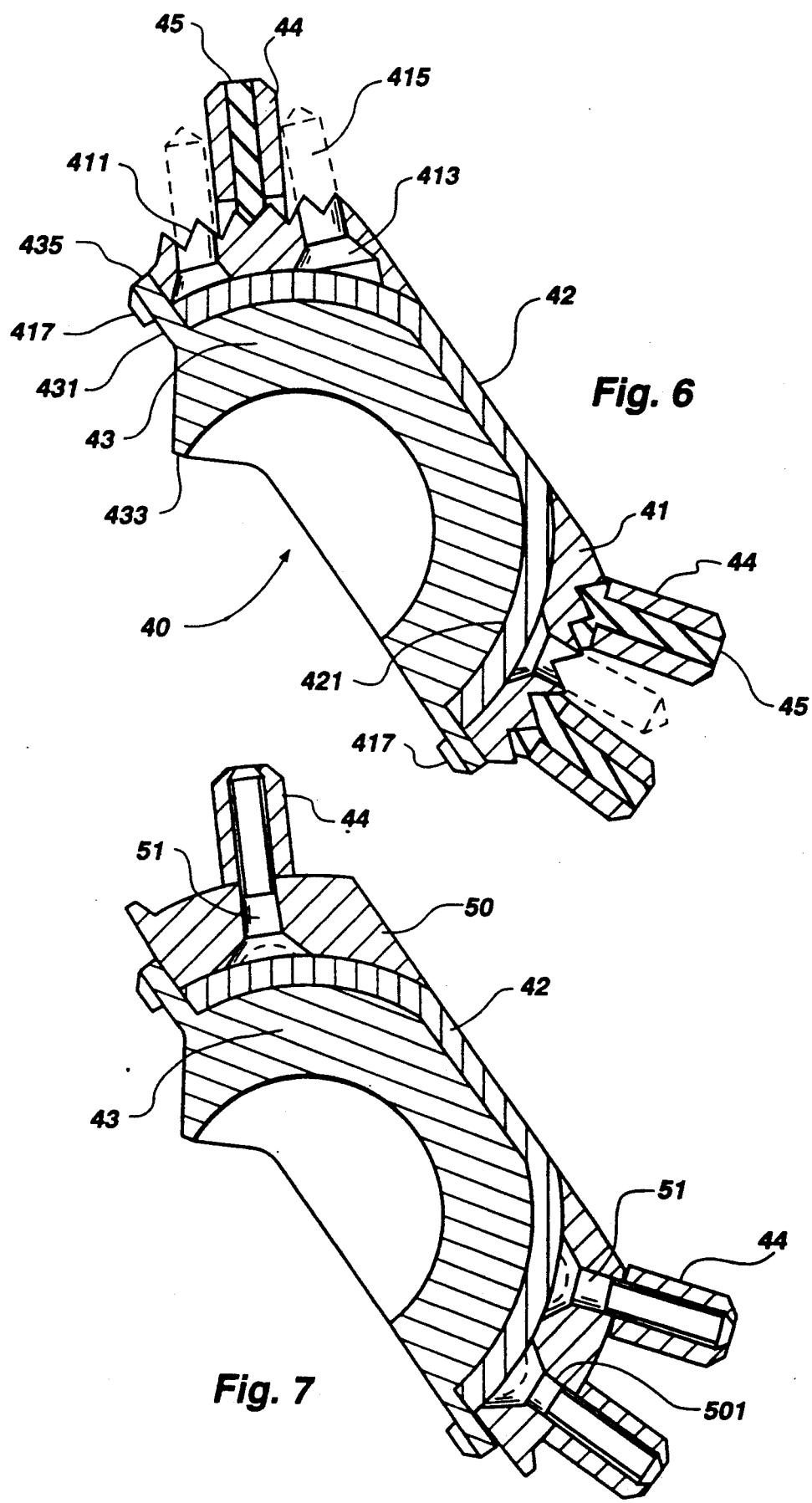

TWO STAGE JOINT PROSTHESIS

This application is a continuation of application Ser. No. 07/240,141, filed Sep. 02, 1988, now abandoned.

The present invention relates to a two stage joint prosthesis and has been developed particularly for use in total hip arthroplasty. As will be clear from the following description, however, the invention is not limited to this particular application. Nevertheless, the invention will be described with particular reference to total hip replacement so that the nature of the invention can be clearly understood.

Total hip replacement was initially reserved for elderly patients with severely debilitating disease. However, the relative success of the operation has lead to its gradual extension to less severely diseased patients and to younger patients. With the extension of the operation to such more active patients, a major problem now exists in the use of this operation for younger and more physically active and sometimes uncooperative or obese patients.

In total hip arthroplasty, the acetabular socket is replaced by a cup of appropriate material and the head and neck of the femur are replaced by an artificial neck and head which articulates within the cup. Both the cup and the artificial neck must be connected to the bone which remains after the diseased components which are to be replaced have been removed. One form of total hip arthroplasty which has been used extensively for around twenty years involves cementing the artificial components to the remaining bone structure.

Total hip replacement prostheses, pioneered by J. Charnley, have been produced by numerous manufacturers and the components commonly available include an ultra high molecular weight polyethylene or ceramic cup and a metal alloy stem with an offset neck and a polished spherical head which articulates with the cup. The cups and stems vary slightly in size and shape and the non metallic cup may be metal backed in order to improve its connection to the bone remaining after excision of the diseased area which the artificial structure is to replace. Under most common present practice, both the cup and the stem are "fixed" to their respective acetabular and femoral bones by self curing polymethyl methacrylate cement.

The major problems with cemented total hip arthroplasty arise at the cement-bone interface. Thus, whilst the cement provides instant rigidity and allows pain free weight bearing soon after the wound heals, loosening at the bone-cement- prosthesis interface (mainly of the femoral component) appears to be inevitable and in anything from two years (in a poorly performed implantation) onwards, may lead to micro movements, to a return of pain to the patient and to the necessity for revision of the replacement surgery. The indications from long time review studies available to date are that, despite the use of better bone preparation and cement techniques, the required revision rate is increasing as the number of younger and more active patients also increases.

The results of revisional surgery are much poorer than for primary surgery. In addition, revisional surgery has a number of substantial hazards such as blood loss, risk of infection and technical failure. Accordingly, cement free systems are being increasingly used in the hope that elimination of cement will permit great longevity. The most advanced of the cement free (cementless) prostheses, which are still in the stage of experimental application, use the combined effect of two techniques of fixation to the bone instead of cement bonding.

The first technique requires that the surface of the stem of the femoral component and the outer face of the acetabular component are manufactured partly smooth and partly roughened. The smooth portion of the stem provides maximal filling of the medullary cavity in order to provide solid initial fixation to cortical or juxacortical cancellous bone while the roughened portion of the stem and that of acetabular component facilitate bone ingrowth into roughenings on the implant surface. Various methods for roughening the implant surface are known including macro interlock, porous coated surfaces achieved by sintering multiple layers of small round cast chrome cobalt spheres to the base stem and metallurgical bonding of titanium alloy fibres to titanium alloy stems. It is most essential, however, when implanting such devices, that a substantial time interval of minimal stress at the prosthesis to the bone contact be allowed in order to promote the rapid ingrowth of cancellous bone tissue. The latter is essential for good stress transfer from the implant to the bone.

The second technique relies on an immediate rigid press fit of the components by appropriate preparation of the femoral medullary cavity with graduated rasps and of the acetabular socket with graduated reamers. Other modifications such as the provision of a stabilizing horizontal platform (collar) for maintaining contact with cortical bone for the femoral component and an outer surface with a self-tapping thread for the acetabular component are also employed.

In a wide number of cases, thigh pain follows cement free hip replacement and is thought to be due to failure of adequate bone ingrowth fixation or of frank micro or macro looseness. However, the success of cement free hip replacements is still very limited and, as indicated above, is dependent upon allowing an adequate time interval of minimal bone stress after the operation has been performed.

Some research indicates that the period of time for ingrowth could be as long as a number of months and the level of stresses which could affect the ingrowth is as little as the stress which occurs when a prostrate patient moves his hip to change its position.

There also is another factor contributing to the rate of loosening the prosthesis components in their respective bone structures. A human hip joint includes in itself a substantial layer of cartilage between the acetabular socket bone and the bone of the head of the femur. The cartilage layer (being at the loaded zone about 4 mm thick) provides low friction articulation of the joint but also presents an elastic dividing medium between bone components of the joint, serving as shock-absorber and damping peak loads at the joint.

Commonly available total hip replacement prostheses lack such an elastic element and provide, especially those with a ceramic acetabular cup, a much stiffer artificial joint than a natural one. Thus more severe peak loads act on all the parts and components of the prosthesis. These peak loads may be considerably high for physically active patients and significantly contribute to loosening of any component of both cemented and cementless prostheses. It is therefore an object of the present invention to provide a prosthesis which will permit cement free joint replacement having substantial improvements over the protheses currently in use. Circumstances, sometimes not related to the performance of an inserted prosthesis (car accident, etc.) or natural wear of the elements of the frictional couple, can cause the necessity for revisional surgery. It is also an object of the present invention to provide a prostheses which has substantial improvements in revision procedure over those currently in use.

Accordingly, the present invention provides in one aspect, a joint prosthesis including two articular parts, characterised in that at least one of said articular parts comprises at least one first stage component and at least one second stage component for implantation at a first stage operation and a second stage operation respectively, said first stage component or components consisting of a surgically insertable structure of appropriate shape and strength to receive eventually at least one second stage component thus creating a composite with sufficient strength and fixation to the bones remaining adjacent the joint replaced by the prosthesis to take the place of the natural elements of the joint being replaced, the first stage component or components including connection means designed to cooperate with connection means of a second stage component, the second stage component forming or supporting at least in part, a bearing surface of the joint prosthesis, and designed so as to be disconnectable as an initial stage of a revision procedure.

More specifically, this aspect of the invention provides a hip joint prosthesis including femoral and acetabular articular parts characterised in that the femoral part comprises three first stage components for implantation at a first stage operation, namely a shaft component for insertion in the medullary cavity of the femoral shaft, a neck component for insertion below the femoral head transverse to the femoral shaft and shaped to lie within a projected tubular surface, and an insert of the neck component turnable within the neck component so that a support portion thereof lies outside said projected tubular surface, and a second stage component for implantation at a second stage operation, comprising portions complementing the first stage shaft and neck components so as to be supported by the said first stage components and further including a head to articulate with the acetabular part.

In another aspect, the present invention also provides a method of total hip arthroplasty characterised in that the method includes a first stage operation wherein a blind hole which is directed supero-medially towards the femoral head and enters the femoral neck within the medulla of the neck is bored in the lateral cortex below the origin of the greater trochanter immediately superior to the inferior cortical bone of the neck and a second blind hole directed downwards to coincide with the central line of the medullary cavity of the superior part of the femoral shaft is bored from the superior aspect of the femur next to the top of the greater trochanter, a first stage shaft prosthetic component of substantially tubular form is inserted through the downward borehole for a predetermined distance into the femoral shaft below the level of the neck of the femur and secured in the shaft, a first stage neck prosthetic component shaped to lie within a projected tubular surface and having an insert of the said neck component confined within the projected tubular surface of said neck component is inserted and secured into the superior part of the femur through the supero-medial borehole, the insert of the neck component is turned to a maximum support position in which a support portion of said insert lies outside the projected tubular surface of the first stage neck component, integration of bone tissue with the inserted first stage components is allowed, and a second stage operation is then performed comprising removing the femoral head and upper part of the superior neck to expose the first stage neck component and the medullary cavity thereby providing a window for insertion of a second stage prosthetic component having a bearing surface to replace the femoral head and including portions complementing the first stage shaft and neck components so that the second stage component is supportable by the first stage components, and inserting the second stage component to its supported position.

Another method aspect of the invention consists of a method of total hip arthroplasty characterised in that the method includes a first stage operation wherein a blind hole which is directed supero-medially towards the femoral head and enters the femoral neck within the medulla of the neck is bored from the superior aspect of the femur next to the top of the greater trochanter, a first stage neck prosthetic component shaped to lie within a projected tubular surface and having an insert of the said neck component confined within the projected tubular surface of said neck component is inserted and secured into the superior part of the femur through the said hole, the insert of the neck component is turned to a maximum support position in which a support portion of said insert lies outside the projected tubular surface of the first stage neck component, integration of bone tissue with the inserted first stage component is allowed, and a second stage operation is then performed comprising removing the femoral head and upper part of the superior neck, boring a blind hole downwards along the central line of the medullary cavity of the superior part of the femoral shaft, inserting a first stage shaft prosthetic component of substantially tubular form through the downward borehole for a predetermined distance into the femoral shaft below the level of the neck of the femur and securing said first stage shaft component in the shaft, and inserting to its supported position a second stage prosthetic component having a bearing surface to replace the femoral head and including including portions complementing the first stage shaft and neck components so that the second stage component is supportable by the first stage components.

As indicated, one aspect of the present invention provides a joint prosthesis including two articular parts, at least one of which articular parts comprises at least two components or sets of components which are adapted to be implanted in a patient in two separate stages or procedures (operations), that is at appropriately spaced times, and which are referred to herein as first stage components and second stage components. At least one first stage component is designed to be implanted before insertion of and attachment thereto of at least one second stage component to form essentially a single structural implant at an appropriate interval after implantation of the first stage component(s).

Each first stage component consists of a surgically insertable structure of appropriate shape and strength to receive eventually the second stage component(s) creating a composite with sufficient strength and fixation to the remaining bones to take the place of the natural elements of the joint being replaced. The shape and the size and also the location and the way of implantation of the first stage component(s) are designed in such a way that the bones and the other related tissues of the joint retain their ability to function as normal after first stage component implantation and the recuperation after the surgical intervention for a prolonged period of time is assured. First stage components are also designed in such a way as not to participate in the load carrying function of the bones of the joint, so that no stresses are induced in the component-to-bone fixation area during normal physical activity.

First stage components are preferably formed of titanium or can be titanium coated, or alternatively may be formed of any biocompatible material which has sufficient strength for its proposed use and is not antagonistic to bone and related tissues. First stage components are preferably formed with a threaded or otherwise roughened bone contact surface to assist initial fixation.

Reseach in the field of dental prostheses has shown that pure titanium implants, due to the chemical properties of the metal, become biochemically integrated with residual bone, which feature herein will be referred to as "osteointegration". It is anticipated that first stage components of the present invention, when being made of titanium or being titanium coated, have the ability of "osteointe- gration".

As was mentioned above, a desirable prerequisite condition for bone ingrowth into an implanted prosthesis is the minimum of stress on bone-to-implant interface for a prolonged period of time. The same is true for the osteointegration process, which takes place best in the absence of this kind of stress.

First stage components include connection means which is designed to cooperate with connection means on second stage components. The connection means on a first stage component may, for example, consist of a recess, optionally threaded, within which a post forming the connection means of a second stage component may be closely inserted.

Second stage components of the invention are also surgically insertable and made of a bio-compatible material of sufficient strength, preferably of a titanium or a cobalt- chromium alloy, and at least one second stage component is adapted to function with a first stage component in the place of the natural components which they are to replace. As mentioned above, at least one second stage component has connection means complementing those of a first stage component. As the second stage component is to form or support, at least in part, a bearing surface of a replacement joint, it will be formed from, fitted with or surfaced with a wear resistant material, for example those types of material already used in joint replacement prostheses. The second stage component in the prosthesis of the invention is thus adapted to cooperate in use with a mating replacement anatomical structure in the total joint which is to be replaced.

At least one second stage component of the invention preferably includes a shock-absorbing insert which is preferably placed between two interlockable elements of the component and is compressed and locked in when the components are assembled in such a way as to distance them and to eliminate their direct contact under load. Alternatively, the shock-absorbing insert can be situated between the first stage component and the second stage component, being locked in and compressed when those components are connected. The shock-absorbing insert may be of a ring- or a cup-like shape and can be formed of a resilient biocompatible material such as silicone polymer.

The second stage component and the connection means are designed in such a way as to be disconnectable without undue effort if revision procedure becomes necessary and to allow the second stage component(s) to be replaced at revision with identical or similar component(s).

For some joints, it may not be possible for one of the two articular parts of the prosthesis to be inserted as a first stage component. For example, in a hip prosthesis, the shape and anatomical struction of the acetabular region of the pelvis does not give access and bone volume sufficient for inserting first stage components, which will provide the required base for the second stage components but not obstruct the continuing function of the joint, before the second stage operation. Accordingly the acetabular part of the hip joint is not replaced in both the first and the second procedures, but in the second procedure only. Therefore, according to present invention, one of articular parts of the prosthesis may not include any first stage component(s), but consist of second stage component(s) only. The term discrete second stage component(s) is used herein to refer to the second stage component(s) mentioned above and inserted independently of any first stage components in the same articular part. Any discrete second stage component is inserted at the second stage operation with the second stage component(s) of the other articular part (which complement the first stage component(s) of the other articular part of the prosthesis which has been in the patient's body since first stage operation).

Any discrete second stage component consists of two relatively different elements or groups of elements. In this embodiment, a first element or group of elements is of the nature described above, that is it is designed to perform the anatomical function of the part of the joint it replaces. Thus the first element or group of elements may be adapted for load bearing and articulation and the term functional second stage component(s) is used herein to refer the such element(s).

Functional second stage components may be subjected to replacement at revision procedure with a similar element/group of elements specially designed for the purpose and herein referred to as revision stage component(s).

A second element or group of elements according to this aspect of the invention are designed to be inserted into the same bone structure as the first element or group of elements, but is designed and inserted in such a way as not to affect the normal performance of the prosthesis and not to participate in the load carrying function of the bones of the joint and of the prosthesis, so that no stresses are induced in the element-to-bone fixation area during normal physical activity. For reasons which will be apparent from the following description, the second element or group of elements is referred to herein as anchoring second stage component(s).

Any anchoring second stage component is preferably formed of titanium or of titanium alloy or can be titanium coated. Each anchoring second stage component includes connection means which is designed to cooperate with connection means of the revision stage component(s) if and after any revision stage component is implanted.

Any anchoring second stage component may, for example, consist of a substantially cylindrical insert threaded outside and having a recess, optionally threaded, within which an anchoring screw or pin may be inserted.

Any revision stage component which also constitutes part of this aspect of the present invention is in design identical to above described functional second stage component(s) with the exception that a revision stage component includes connection means complimenting those of the second stage anchoring component(s) and can be designed larger in dimensions allowing additional bone trimming at the revision procedure. The connection means of the revision stage component(s) preferably comprise anchoring screws or pins.

In order to assist a further understanding of the present invention, the application of the invention to a total hip replacement will be described below in some detail. It is to be understood that the following description represents a preferred embodiment only of the present invention and is given by way of illustration, not limitation.

A joint prosthesis according to the present invention designed for human total hip replacement comprises two articular parts—femoral and acetabular. The femoral part of the prosthesis preferably includes three first stage components—the shaft component, the neck component and the insert of the neck component, and an integral or composite second stage component. To insert the first stage components, an initial (first stage) operation is performed which comprises (i) boring a blind hole in the lateral cortex below the origin of the greater trochanter which is directed supero-medially towards the femoral head and enters the femoral neck within the medulla of the neck immediately superior to the inferior cortical bone of the neck (precise direction of the hole both antero-posteriorly and supero-inferiorly can be facilitated by using a guide wire and x-ray image intensifying equipment) and (ii) boring a blind hole from the superior aspect of the femur (next to top of the greater trochanter) directed downwards to coincide with the central line of the medullary cavity of the superior part of the femoral shaft.

A first stage shaft component of substantially tubular form is inserted through the downward borehole for a predetermined distance into the femoral shaft below the level of the neck of the femur and secured in the shaft. A first stage neck component having a cylindrical or a tapered outer surface and an insert of the neck component confined within this outer surface is inserted and secured into the superior part of the femur through the supero-medial borehole with the insert of the neck component being properly aligned later on. Both the shaft and the neck inserted components have hollow internal portions which may be filled with a biocompatible plastic material to prevent the ingress of tissue in the period of time to performing the second stage of the operation. The medullary femoral cavity between the components may also be filled with biocompatible plastic material.

Following implantation of the first stage components, the incisions required for their insertion are closed. As the hip joint itself has not been opened, the patient may continue physical activity until such time as the second stage of the replacement operation is performed.

After implantation of the first stage components, osteointegration of bone tissue with the exterior of the implanted components will occur and can be demonstrated by radiological and clinical methods. When integration of the bone tissue is judged to be sufficient the second stage of the operation is performed. The femoral head and upper part of the superior neck are removed to expose the first stage neck component and the medullary cavity and to provide a natural window for insertion of a second stage component. Prior to insertion of the second stage component, any filler is removed from the interior of the first stage components and the medullary cavity is enlarged if necessary.

The second stage component includes portions complementing the first stage shaft and neck components so that the second stage component is supported by the first stage components. The second stage component may be formed with a connectable head to articulate with an acetabular component, or the head may form an integral part of the second component. After inserting the second stage component, it is preferably secured to the femur by means of anchoring screws.

The above described method of two stage implantation of the prosthesis is supposed to be the most common one. However, due to medical or other reasons, an alternative method of implantation of the prosthesis can be employed, and the decision as to which method to use is that of the surgeon.

In the proposed alternative method of implantation of the prosthesis, the first stage neck component, together with the insert of the neck component only are actually inserted at the first stage operation in the prepared supero-medial borehole. No downward hole from the superior aspect of the femur is bored, and no insertion of the first stage shaft component takes place, at the first stage operation.

After the period of time allowed for osteointegration of the first stage neck component and its insert, the second stage of the operation is performed.

At the second stage operation the femoral head and upper part of superior neck are removed and a blind hole is bored downwards along the central line of the medullary cavity of the superior part of the femoral shaft in a manner very similar to that described above.

As a continuation of the second stage operation by the alternative method, the first stage shaft component is inserted through the downward borehole for a predetermined distance into the femoral shaft in a manner described above.

The second stage component is inserted into the osteointegrated first stage neck component and into the first stage shaft component immediately after insertion of the first stage shaft component.

This alternative method of the prosthesis implantation has certain advantages as it significantly simplifies and reduces the scale of the first stage operation, leaving the second stage operation mostly of the same complexity.

The shortcoming of the alternative method of implantation is the lack of a stress-free osteointegration process for the first stage shaft component (because of its inserting at the second stage operation). The first stage shaft component may be subjected to loading stresses from the moment of its implantation. However, the shaft component may be very firmly secured against the loads acting on it in the medullary cavity of the femoral shaft by mechanical means, for example, by selftapping it into cortical bone.

The acetabular part of the total hip joint prosthesis can be inserted in a conventional manner at the second stage of the operation as it presently appears that this component of a total hip joint prosthesis causes very much less of a problem than does the femoral component.

The acetabular part preferably comprises an acetabular ring formed of metal of a sufficient strength, preferably of a titanium or a cobalt-chromium alloy, an acetabular cup formed of a low-friction material, preferably of UHMW polyethylene or aluminum oxide ceramics, and, in accordance with a preferred form of this invention, a shock-absorbing insert made of bio-compatible resilient material such as silicone polymer. Both the acetabular ring and the acetabular cup have a locking arrangement between them mutually locating them and preventing them from angular displacement and from moving apart one from another, but (in the preferred embodiment which includes the shock-absorbing insert) allowing their movement one toward another. Preferably the shock-absorbing insert is locked and compressed between the acetabular ring and cup transferring load from one to another.

All three components in the preferred form of acetabular part are hollow solids of revolution and the external surface of the acetabular ring corresponds to the surface of the cavity reamed in the acetabular bone, while the internal surface of the acetabular cup corresponds to the spherical surface of the femoral component head. The shock-absorbing insert is of a complementary design with its outer surface corresponding to the internal surface of the acetabular ring while the internal surface of the shock-absorbing insert corresponds to the external surface of the acetabular cup.

It should be clearly understood that in some cases the femoral part of the invention may be used with an acetabular part not including this shock-absorbing insert and comprising the acetabular ring and acetabular cup or comprising the acetabular cup only, and that does not significantly diminish the advantages of the primary invention.

The acetabular part preferably comprises also a number of anchoring inserts made of titanium or of titanium alloy or titanium coated. Each of these inserts has a hollow internal portion which may be filled with a bio-compatible plastic material to prevent the ingress of tissues. The anchoring inserts, when used, are imbedded into the acetabular bone structure after the final preparation of the acetabular ring seat until they are level or deeper than the seat surface. The rest of the acetabular component(s) is inserted after and over the anchoring inserts in such a way as not to be supported by or connected to inserts, but may be secured by separate means such as bone screws. By following this technique at the second stage of the primary operation the basis for successful revision of the acetabular component(s) is established.

At revision operation, should it become necessary, not only the acetabular cup and the shock-absorbing insert can be replaced, but the acetabular ring also. The replacement acetabular ring may be secured, unlike the original one, with connection means to the anchoring inserts implanted at the primary operation and osteointegrated into acetabular bone.

To further illustrate the present invention, reference is now made to the accompanying drawings showing one preferred form each of components for a femoral prosthesis part and for an acetabular prosthesis part respectively. It is to be appreciated that the illustrated prosthesis has been designed for optimum performance and that various features are merely preferred to achieve this optimum. Such features may be varied without departing from the present invention. It is also stressed that the illustrated prostheses represent only presently preferred embodiments of the invention and are not to be taken as limiting the scope of the invention broadly described herein.

In the drawings FIGS. 1 to 5 show the femoral articular part of the prosthesis, FIGS. 6 and 7 show acetabular articular part of the prosthesis. In particular:

FIG. 2A is a plan view of an insert for the first stage neck component of FIGS. 1A to 1F;

FIGS. 2B to 2E are elevation views of the insert of FIG. 2A;

FIG. 3A is an elevation view of a first stage shaft component;

FIG. 3B is a plan view of the component of FIG. 3A;

FIG. 3C is a section view on the line IIIC—IIIC of FIG. 3A;

FIG. 4A is a front elevation of a second stage component;

FIG. 4B and 4D are plan and inverted plan views of the component of FIG. 4A;

FIG. 4C and 4E are opposite side elevations of the component of FIG. 4A;

FIG. 5A is a front view of the full femoral articular part of the prosthesis in position in the left femur as viewed from the rear of the body and including all the components of FIGS. 1 to 4;

FIG. 5B is a left hand side view corresponding to FIG. 5A;

FIG. 5C is a top view corresponding to FIG. 5A;

FIG. 5D is a rear view corresponding to FIG. 5A;

FIG. 5E is a bottom view corresponding to FIG. 5A;

FIG. 5F is a right hand side view corresponding to FIG. 5A;

FIG. 6 is a cross section of an assembled acetabular part of the prosthesis as inserted in an initial acetabular replacement operation; and FIG. 7 is a cross section of an assembled acetabular part of the prosthesis as inserted in a revision operation.

Figure 1B:
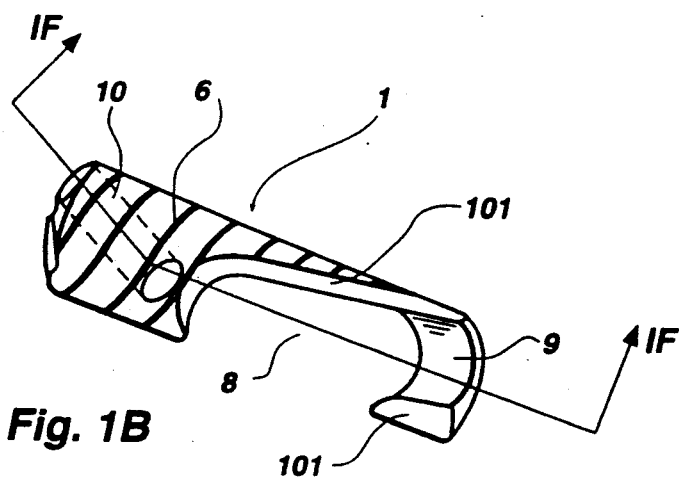
FIGS. 1B to 1E are elevation views of the component of FIG. 1A.
Figures 1A, 1C, 1E:
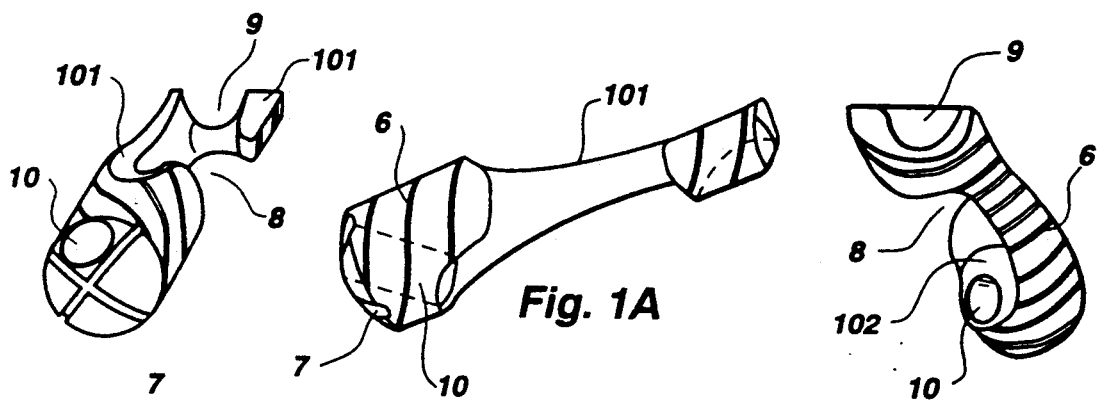
FIG. 1A is a plan view of a first stage neck component.
Figure 1D:
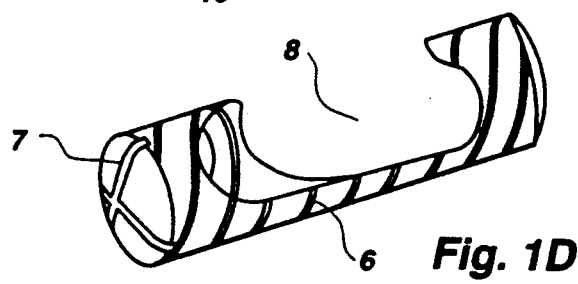
Figure 1F:
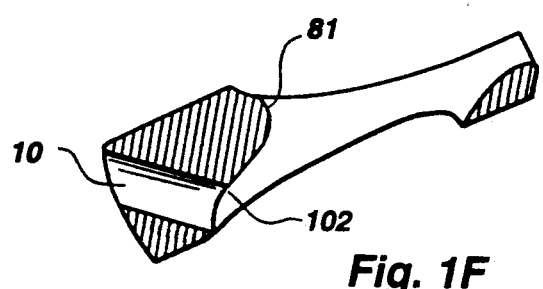
FIG. 1F is a section view on the line IF—IF of FIG. 1B.

The first stage neck component of FIG. 1 is designed for implantation, as shown on FIG. 5, from below the greater trochanter and through the neck of the femur up to the femoral head and is thus referred to below as a subtrochantero-cervical bar or STC bar.. The STC bar is preferably made of titanium or titanium coated.

The subtrochantero-cervical bar 1 (See also FIG. 5) is of generally cylindrical or tapered form and is located latero-medially, infero-superiorly at an angle less than that of the femoral neck 2 to the femoral shaft 3. The STC bar 1 is inserted through a bore which starts immediately below the greater trochanter 4 and is directed into the femoral neck 2 in such a way that it passes next to the inferior cervical cortical bone 5.

The anteversion angle of the STC bar 1 when positioned inside the bore is greater than that of the femoral neck 2, which facilitates a more central STC bar location in the proximal femur.

The STC bar 1 (see FIG. 1) has an external thread 6 which facilitates anchoring of the STC bar 1 in bone and a socket 7 at its lateral end which allows it to be screwed into the bone. Threads 6 are left-handed if bar 1 is to be inserted in a left femur, right-handed if bar 1 is to be inserted into a right femur. The STC bar has a posterior recess 8 in its middle part which is directed vertically and an axial recess 9 in the cervical end of the STC bar opened superiorly and running from the posterior recess 8 medially. The anteversion angle of the long axis of the posterior recess 8 and that of the axial recess 9 when the STC bar is positioned inside the bone is equal to or greater than that of the femoral neck.

The supero-medial part of STC bar is machined off leaving a spheroidal seat 101. The STC bar 1 also has a bore 10 running from its lateral end and entering the posterior recess 8 with a part-spherical seat 102 at its entry point. The direction of the bore 10 is postero-inferiorly, from the superior lateral part of the STC bar 1.

The bore 10 houses a supportive insert 11 (FIG. 2). The supportive insert 11, which is preferably made of titanium or titanium coated has a shallow hook-shaped body 12 including part-spherical shoulder end 115 next to a protruding cylindrical stem 13. Stem 13 is directed at an angle to the body 12 and has a socket at its free end. The entire body of the supportive insert 11 is confined within a surface of revolution which has its axis coinciding with that of the stem 13. Insert 11 is adapted to be rotatably located in the bore 10.

The angle of the bore 10 (FIG. 1) and the shape of the insert 11 (FIG. 2) allows the latter to have two extreme positions: an internal one, in which the insert 11 does not protrude beyond the contours of the STC bar 1 and an external one, in which the insert 11 is maximally protruding outside of the STC bar.

The internal and external positions of the insert 11 are reached by rotating the stem 13 within bore 10 (see FIG. 1 and 2). At the internal position, the hook-shaped body 12 of insert 11 is contained within the posterior recess 8 of the STC bar 1 and does not extend outwardly beyond the projected external surface of the bar. Bar 1 can thus be readily inserted through the open end of the bore located immediately below the greater trochanter when insert 11 is in its internal position.

When drilling the femur to shape the bore for insertion of the STC bar, a special cavity 105 (see FIG. 5) is carved from inside the bore through its wall into surrounding bone with a dedicated tool. This cavity is located postero-inferiorly to the bore beneath the greater trochanter close to the lateral cortical bone 106 and is cut to accomodate the insert 11 in its external position. After insertion of bar 1 with insert 11 in its internal position, stem 13 of insert 11 is rotated within bore 10 and the insert is turned to its external position as shown on FIG. 5. Insert 11 has an external thread 15 at its cylindrical surface which cuts into the surrounding bone when insert 11 is turned, after insertion of bar 1, to its external position. Thread 15 is so directed as to press spherical shoulder 115 of the insert 11 into contact with the seat 102 (FIG. 1) formed in the STC bar, when the insert 11 is rotated to its external position.

The hook-shaped body 12 of insert 11 has a concave surface 14 which in the external position makes a continuation of the lateral end of the posterior recess 8 of the STC bar 1.

The first stage shaft component 30 (see FIG. 3) is inserted most commonly as part of the first stage operation, or alternatively at the second stage operation: It is of tubular shape and can be open at both ends or with a closed and shaped bottom end and is referred to hereafter as supporting bush 30. Supporting bush 30 is inserted through the bore directed downwards from close to the tip of the greater trochanter to provide a diaphyseal support for the second stage component 20.

Supporting bush 30 has an internal longitudinal bore 31, and the outside of the bush 30 has an external thread 305 to allow it to be screwed into the bone of the femoral shaft. The inferior end 33 of the support component 30 is tapered to facilitate its self-tapping into the bone. The superior end 34 of the support component 30 has slots 35 for the driving tool used to screw the support component 30 into the femoral shaft.

The supporting bush 30 is preferably made of titanium or titanium coated and an antiseizing coating could be applied to the bore 31 of the supporting bush and/or to the tail part of the second stage components. Alternatively, the supporting bush 30 can be made of material different from and making a low-friction couple with the material of the second stage component, for example, from UHMW polyethylene or aluminium oxide ceramic.

The second stage component 20 as shown in FIG. 4, includes a main stem 21 which merges with a neck 22 to which ball head 23 is connected. The upper part of main stem 21 forms collar 24 having a part-spheroidal lower face 25 which rests, in the assembled position, on the STC bar 1. The main stem 21 includes a curved middle body portion 26 which is adapted to pass through the posterior recess 8 in STC bar 1 (FIG. 1). Main stem 21 is tapered downwardly and is formed at its lower end as an ovoid shaped tail 27 adapted to rest within supporting bush 30 (FIG. 3).

As illustrated, the ball head 23 has an internal Morse taper to facilitate a reliable connection with the corresponding external taper of the neck 22. Ball head 23 is preferably formed separately to assist manufacturing procedures but may be integral with the remainder of component 20 if desired.

Neck 22 has a Morse taper and is directed superiorly when main stem 21 is implanted. A longitudinal axis of the neck 22 extends at approximately 45 degrees to the longitudinal axis of main stem 21. The collar 24 of the main stem is limited superiorly by a curved surface 241 which starts at the highest point of the base of the neck, tangentially to the surface of the neck. This surface runs laterally and turns superiorly just medially to the greater trochanter, forming a trochanteric plate 28. The trochanteric plate 28 extends superiorly out of the collar 24, and when in use contacts the medial border of the greater trochanter 4 at 403 (FIG. 5) which can be trimmed to ensure good contact with the plate. The outer contour 281 of the trochanteric plate 28 in general corresponds to that of the greater trochanter with an optional intermediate notch 29 for the tendons of the obturator muscles, shown in dotted lines at FIG. 4. The trochanteric plate 28 at its posterior area has at least one countersunk hole 282 for a securing cortical screw, while at the anterior area the trochanter plate has a number, but preferably two similar holes 283 for securing screws, with all the screws passing laterally through the substance of the greater trochanter to reach its lateral cortical bone.

Securing the trochanteric plate 28 to the bone assists in distribution of the loads between the prosthesis and the remaining structure of the femur more similar to natural load distribution, causing the greater trochanter 4 (FIG. 5) and its surrounding structure to carry partially the bending component of the load applied to the prosthesis. In addition to that, securing the trochanteric plate 28 to the cortical trochanteric bone structure assists in securing the main stem 21 against upwards movement out of STC bar 1 and supporting bush 30.

The collar 24 is limited inferiorly by a spheroidal surface of the lower face 25 starting next to the horizontal diameter 221 of the base of the neck and running laterally with a downward slope, meeting the trochanteric plate 28 and ending laterally to its inferior end and forming a rounded, latch-shaped projection 241. The seat 101 of the STC bar (FIG. 1) supports the lower face 25 of the collar 24 of the second stage component 20 with the possibility of angular and laterally-medial self-alignment of component 20. The anterior 242 and posterior 243 borders of the collar 24 generally follow the outlines of the STC bar 1, but are preferably wider by the thickness of the cortical bone. The anterior and posterior borders of the collar 24 blend in use of the prosthesis with corresponding borders of the cortical bone of the inferior part of the femoral neck, which is not removed during the operation, while the top 244 of the collar 24 is much flatter than the profile 245 (FIG. 5) of the femoral neck, thus leaving free space (bounded laterally by the trochanteric plate 28) for the superior border of the acetabular cup in full abduction.

The anterior outline of the collar 24 has at least one notch 246 shown just medial to the trochanteric plate 28. This notch 246 may be used alone or in conjunction with other notches and/or projections not shown, to assist in the removal of component 20. Removal of component 20 may be necessary if revision of the prosthetic implant becomes necessary. In this event, it is desirable to provide means such as notch 246 which can minimise trauma to the patient during removal of component 20 by being engaged with a special tool which uses the medial end of the STC bar 1 as fulcrum.

The lateral latch-shaped projection 241 has an internal radius 247 blending it with the lateral side of the main stem 21. This radius is supported by the external radius 81 at FIG. 1, blending the top part-spheroidal face of the STC bar 1 and the lateral extremity of the posterior recess 8 of the STC bar. The body of the main stem 21 on horizontal cross-section is sausage-shaped, corresponding to the horizontal cross-section of the posterior recess 8 of the STC bar (FIG. 1).

The body of the main stem 21 is curved in the shape of a half-arch, so that in use the axis of the inferior part and the tail is on the long axis of the femoral shaft, while the central curve of the superior part blends with the axis of the neck. The anteroposterior thickness of the concave part 261 of the middle body portion 26 is smaller than that of the rest of the portion, to allow that part of the stem to be inserted into the axial recess 9 of the STC bar 1 (FIG. 1) The axial recess 9 of the STC bar 1 supports the thinner part 261 of the stem against rotation about its vertical axis. The surface 14 of the insert 11 together with the lateral end of posterior recess 8 of the STC bar 1 form a concave support for the convex lateral side of the main stem 21 of the second stage component 20.

In use, the main stem 21 is placed in and oriented by the posterior and the axial recesses 8, 9 of the STC bar 1, acquiring the anteversion angle of the long axis of the posterior recess 8 and of the axial recess 9. As this angle is equal to or greater than the anteversion angle of the femoral neck, the correct orientation of the ball head is achieved. The greater anteversion angle of the prosthesis may be necessary to compensate for the effects on the position of the main stem 21 due to the anterior convexity of the femoral shaft. The taper angle of the lateral contour 201 of the main stem 21 inferiorly is greater than that of the opposite medial contour to allow for the natural shape of the femoral shaft and to facilitate insertion and removal of the main stem 211 through the window naturally formed after the removal of the femoral neck and head.

Most external parts of the inferior surfaces of collar 24 which will not, in use, be supported by contact with the seat 101 of the STC bar 1 (FIG. 1) are preferably formed with a roughened or sharpened surface, as by high profile knurling, as shown at 248 on FIG. 4. These sharpened surfaces will enable component 20 to cut through any residual bone which may have been left adjacent STC bar 1 and which would otherwise interfere with the seating of component 20 on the bearing surfaces of bar 1.

The tail 27 (the lowest part of the main stem 21) is shaped as an elongated ovoid surface of rotation which starts as a smaller diameter neck and below its largest diameter is tapered down to an end. The greatest diameter of the tail 27 makes a light interference fit with the internal diameter of the diaphyseal supporting bush 30 (FIG. 3). This way of supporting the tail 27 allows for angular and longitudinal disalignment resulting from deviations in placement of both parts into the bone.

The acetabular articular part of the prosthesis is designed for implantation into the lateral wall of the pelvis. In particular this part is imbedded into the cavity of the acetabulum which is shaped with special tools to correspond to the external configuration of the part.

The acetabular articular part is shown in FIGS. 6 and 7, where FIG. 6 shows the cross section of a unitary set of functional and anchoring acetabular components for insertion in succession, all at the second stage of the primary operation, while FIG. 7 shows the cross section of the revision acetabular components for insertion at the revision operation.

The acetabular part 40 of the prosthesis for insertion at primary operation consists of the acetabular ring 41, the shock-absorbing insert 42, the acetabular cup 43, and the anchoring inserts 44 with plugs 45.

The acetabular ring 41 is a solid of revolution and has surface 411 which is semi-spheroidal or tapered or a combination of both. The acetabular ring 41 can be annular, as shown in the FIG. 6 cross section, or can continue to a closed form.

The external surface 411 of the acetabular ring is adapted to provide reliable securing in the bone and may be of porous or roughened nature to assist bone ingrowth, may have antitorsional pegs or alternatively, as shown, it can have an external thread, preferably self tapping. As additional means of securing the ring to the bone, the ring can have a number of countersunk holes 413 in it for accomodating retaining screws 415. The medial-inferior face of the ring 40 is fitted with locking means 417 adapted to cooperate with locking means on the acetabular cup 43. The internal surface of the ring 41 forms a cavity of a preferably semi-spherical shape to accomodate the internal elements of the acetabular part 40.

The shock-absorbing insert 42 is of semi-spherical cup-like shape and its external surface corresponds to the internal surface of the ring 41, while its internal surface 421 is preferably of semi-spherical shape with the thickness of the shock absorbing insert being preferably constant or near-constant. The shock-absorbing insert 42 is formed of resilient material with emphasis on the elastic and energy-dissipation properties of the material.

The acetabular cup 43 is of a conventional design and has a semispherical shape with its external surface corresponding to the internal surface 421 of the shock-absorbing insert 42. The internal surface of the acetabular cup 43 is a part of a sphere, corresponding to that of the ball head 23 (FIG. 4).

The acetabular cup 43 can have a restricting collar 431 and a supero-medial projection 433. The acetabular cup is fitted with locking means 435 which interact with the locking means 417 of the acetabular ring 41.

The cross section of the shock-absorbing insert 42 is chosen in such a way that after assembly and locking together of the acetabular cup 43 and the acetabular ring 41, insert 42 is compressed in the recess formed by the internal surface of the ring 41 and the cup 43. The locking means 417 of the acetabular ring 41 and the locking means 435 of the acetabular cup 43 are designed in such a way as to prevent their disconnection and mutual angular displacement but to permit their moving closer under load with resulting further compression of the shock-absorbing insert 42.

To insert the acetabular ring 41, the acetabulum is reamed with properly oriented reamers of the size and shape of the ring. It is after this step of the primary operation that the anchoring inserts 44 may be implanted, before placing the acetabular ring 41 in its place.

The anchoring inserts 44 are of cylindrical or tapered shape with a threaded external surface and have a slot for the driving tool (not shown) at the end for screwing all the inserts into holes drilled with a special template. The location and the depth of insertion of the inserts 44 are such as to clear the acetabular ring 41 in its installed position and to clear its retaining screws 415. Each insert 44 has an internally threaded bore filled with removable plugs 45 of material such as biocompatible plastic to prevent ingrowth of tissue.

The revision stage acetabular components shown at FIG. 7 are of a design very similar to the acetabular components described above but the replacement acetabular ring 50 can be larger in outside dimensions to allow for additional reaming in the process of revision and may not be threaded on the outside. The replacement acetabular ring 50 has screw holes 501 located so as to coincide with holes of the inserts 44 and to enable screws 51 to be threaded into the inserts.

The design of the acetabular part of the prosthesis allows for the fixation of the revision stage acetabular components of the prosthesis, similar to fixation of the second stage component of the femoral part of the prosthesis, by connecting the revision stage acetabular components to the anchoring inserts implanted at the second stage of the primary operation and osteointegrated with the bone structure.

The present invention thus provides a prosthesis which can be used in a two stage implantation procedure which will allow osteointegration of at least one element of the first stage implant with the adjacent bone structure prior to the completion of the total replacement procedure. A patient can resume the activity available prior to the implantation of the first stage component while osteointegration occurs and the second stage of the replacement procedure can then be performed to produce a total replacement which overcomes the disadvantages of the present prostheses and provides a long lasting total joint replacement. For the part(s) of the prosthesis to be implanted strictly at the second stage of the replacement procedure, the present invention provides the means, if a revision procedure is required, of replacement with revision part(s) having the full advantages of two-stage osteointegrated implantation structure.

As indicated above, the specific description has referred primarily to the replacement of hip joints. It will be appreciated however that the prosthesis of the present invention can be applied to other joint replacements where the advantages of the two stage replacement procedure described above will be obvious to those skilled in the art.

We claim:

1. A hip joint prosthesis including femoral and acetabular articular parts characterized in that the femoral part comprises:

three first stage components for implantation at a first stage operation without opening the hip joint, a second stage component for implantation at a second stage operation, and a head component to articulate with the acetabular part;

said first stage components consisting of an elongated neck component for insertion in the lateral cortex of the femur below the femoral head and transverse to the femoral shaft, said neck component including an insert housing portion, comprising an internally directed bore, and a recessed support portion configured to engage the femur below the greater trochanter through the neck of the femur along the inferior cervical cortical bone said neck component being shaped to define a projected tubular surface; an insert of the neck component housed within the neck component and turnable therein so that a support portion of said insert lies outside said projected tubular surface, and a shaft component for insertion in the medullary cavity of the femoral shaft remote from said neck component and said insert of the neck component;

said second stage component comprising (i) a tail portion complementing the first stage shaft and neck components so as to be supported by said first stage shaft component, (ii) a collar portion complementing the first stage neck components so as to be supported by said first stage neck components; (iii) a stem portion connecting the tail portion and the collar portion by merging at its opposite ends with said tail portion and said collar portion, and (iv) a neck portion merging with said collar portion transversely to the merger of said collar portion through the stem portion with said tail portion and connectable to said head component.

2. A hip joint prosthesis as claimed in claim 1 wherein the acetabular part comprises an acetabular metal ring, an acetabular cup formed of low friction material, and a locking means for mutually locating the ring and cup and preventing their relative angular displacement and movement apart from one another.

3. A hip joint prosthesis as claimed in claim 2 wherein the acetabular part further includes a shock-absorbing insert made of bio-compatible resilient material capable of being locked and compressed between the acetabular ring and the acetabular cup and wherein the locking means allows axial movement of the ring and cup one toward another.

4. The hip joint prosthesis of claim 1 wherein the acetabular part also comprises a plurality of anchoring inserts each having a hollow internal portion, each said insert being adapted to be imbedded into the acetabular bone structure prior to insertion of the remaining acetabular components.

5. The hip joint prosthesis of claim 2 wherein the acetabular part also comprises a plurality of anchoring inserts each having a hollow internal portion, each said insert being adapted to be imbedded into the acetabular bone structure prior to insertion of the remaining acetabular components.

6. The hip joint prosthesis of claim 3 wherein the acetabular part also comprises a plurality of anchoring inserts each having a hollow internal portion, each said insert being adapted to be imbedded into the acetabular bone structure prior to insertion of the remaining acetabular components.

7. A hip joint prosthesis including femoral and acetabular articular parts characterized in that the femoral part comprises:
   three first stage components for implantation at a first stage operation without opening the hip joint,
   a second stage component for implantation at a second stage operation, and
   a head component to articulate with the acetabular part;
   said first stage components consisting of an elongated neck component for insertion below the femoral head transverse to the femoral shaft, said neck component including an insert housing portion, having an internally directed bore, and a recessed support portion configured to engage the femur below the greater trochanter through the neck of the femur along the inferior cervical cortical bone said neck component being shaped to lie within a projected tubular surface, and an insert of the neck component rotatably housed within the neck component so that a support portion of said insert lies outside said projected tubular surface; and a shaft component for insertion in the medullary cavity of the femoral shaft remote from said neck component and said insert of the neck component;
   said second stage component comprising (i) a tail portion complementing the first stage shaft and neck components so as to be supported by said first stage shaft component, (ii) a collar portion complementing the first stage neck components so as to be supported by said first stage neck components, (iii) a stem portion connecting the tail portion and the collar portion by merging at its opposite ends with said tail portion and said collar portion, by merging at its opposite ends with said tail portion and said collar portion, and (iv) a neck portion merging with said collar portion transversely to the merger of said collar portion through the stem portion with said tail portion and connectable to said head component.

8. A hip joint prosthesis as claimed in claim 7 wherein the acetabular part comprises an acetabular metal ring, an acetabular cup formed of low friction material, and a locking means for mutually locating the ring and cup and preventing their relative angular displacement and movement apart from one another.

9. A hip joint prosthesis as claimed in claim 8 wherein the acetabular part further includes a shock-absorbing insert made of biocompatible resilient material capable of being locked and compressed between the acetabular ring and the acetabular cup and wherein the locking means allows axial movement of the ring and cup one toward another.

10. A hip joint prosthesis as claimed in claim 7 wherein the acetabular part also comprises a plurality of anchoring inserts each having a hollow internal portion and adapted to be imbedded into the acetabular bone structure prior to insertion of the remaining acetabular components.

11. A hip joint prosthesis as claimed in claim 8 wherein the acetabular part also comprises a plurality of anchoring inserts each having a hollow internal portion and adapted to be imbedded into the acetabular bone structure prior to insertion of the remaining acetabular components.

12. The hip joint prosthesis of claim 9 wherein the acetabular part also comprises a plurality of anchoring inserts each having a hollow internal portion and adapted to be imbedded into the acetabular bone structure prior to insertion of the remaining acetabular components.

13. A hip joint prosthesis including femoral and acetabular articular parts characterized in that the femoral part comprises:
   three first stage components for implantation at a first stage operation without opening the hip joint;
   a second stage component for implantation at a second stage operation; and
   a head component to articulate with the acetabular part;
   said first stage components consisting of an elongated neck component for insertion below the femoral head transverse to the femoral shaft, said neck component including an insert housing portion having an internally directed bore, and a recessed support portion configured to engage the femur below the greater trochanter through the neck of the femur along the inferior cervical cortical bone, said neck component being shaped to lie within a projected tubular surface, and an insert of the neck component rotatably housed within the neck component so that a support portion of said insert lies outside said projected tubular surface; and a shaft component for insertion in the medullary cavity of the femoral shaft remote from said neck component and said insert of the neck component;
   said second stage component comprising (i) a tail portion supportable by said first stage shaft component, (ii) a collar portion, (iii) a stem portion connecting the tail portion and the collar portion and (iv) a neck portion connected to said collar portion transversely to said stem portion, said neck portion being connectable to said head component.

* * * * *